US00PP35480P2

(12) United States Plant Patent
Tashiro

(10) Patent No.: US PP35,480 P2
(45) Date of Patent: Nov. 14, 2023

(54) BIDENS PLANT NAMED 'BALBIDBADOR'

(50) Latin Name: *Bidens ferulifolia*
Varietal Denomination: Balbidbador

(71) Applicant: Ball Horticultural Company, West Chicago, IL (US)

(72) Inventor: Rebecca M. Tashiro, Nipomo, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/132,656

(22) Filed: Apr. 10, 2023

(51) Int. Cl.
*A01H 5/02* (2018.01)
*A01H 6/14* (2018.01)

(52) U.S. Cl.
USPC ..... Plt./410

(58) Field of Classification Search
USPC ..... Plt./410
See application file for complete search history.

*Primary Examiner* — Susan McCormick Ewoldt
(74) *Attorney, Agent, or Firm* — Audrey Charles

(57) ABSTRACT

A new and distinct cultivar of *Bidens* plant named 'Balbidbador', characterized by its double-type, dark red-orange and yellow-orange bicolored inflorescences, medium green-colored foliage, and moderately vigorous, compact, semi-upright growth habit, is disclosed.

1 Drawing Sheet

Latin name of genus and species of plant claimed: *Bidens ferulifolia.*

Variety denomination: 'Balbidbador'.

BACKGROUND OF THE INVENTION

The present invention relates to a new and distinct cultivar of *Bidens* plant botanically known as *Bidens ferulifolia* and hereinafter referred to by the cultivar name 'Balbidbador'.

The new cultivar originated in a controlled breeding program in Guadalupe, California during May 2019. The objective of the breeding program was the development *Bidens* cultivars that have double-type inflorescences, large inflorescences with attractive coloration and moderately vigorous, compact, semi-upright growth habit.

The new *Bidens* cultivar was the result of a self-pollination of the proprietary *Bidens ferulifolia* breeding selection coded BID-1490-002, not patented, characterized by its semi-double type, medium orange and light orange bicolored flowers, medium green-colored foliage, and vigorous, semi-upright growth habit. The new cultivar was discovered and selected as a single flowering plant within the progeny of the above stated self-pollination during October 2020 in a controlled environment in Guadalupe, California.

Asexual reproduction of the new cultivar by terminal stem cuttings since October 2020 in Guadalupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balbidbador' as a new and distinct cultivar of *Bidens* plant:

1. Double-type, dark red-orange and yellow-orange bicolored inflorescences;
2. Medium green-colored foliage; and 3. Moderately vigorous, compact, semi-upright growth habit.

Plants of the new cultivar differ from plants of the parent primarily in having a more ray florets per inflorescence, a more compact growth habit and reduced growth vigor.

Of the many commercially available *Bidens* cultivars, the most similar in comparison to the new cultivar is Sun Drop Double Yellow 'Balbisdel', not patented. However, in side-by-side comparisons, plants of the new cultivar differ from plants of 'Balbisdel' in at least the following characteristics:

1. Plants of the new cultivar have red-orange colored ray florets that is different from the solid, yellow-colored ray florets of plants of 'Balbisdel'; and
2. Plants of the new cultivar have a semi-upright growth habit that is different from the mounded growth habit of plants of 'Balbisdel'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'Balbidbador'. The plants were approximately 5-months old. The plants were grown in 4.5-inch containers for approximately 4 months in a greenhouse in West Chicago, Illinois. Plants were given one pinch at transplant.

DETAILED BOTANICAL DESCRIPTION

Figure 1:
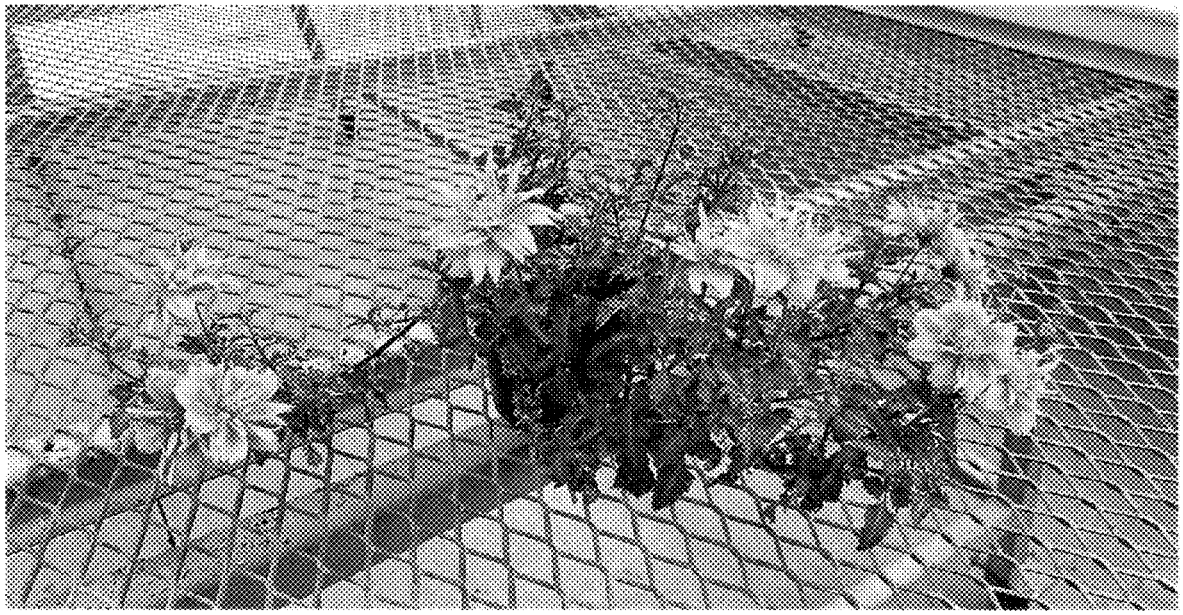
FIG. 1 illustrates a side view of the overall growth and flowering habit of 'Balbidbador'.
Figure 2:
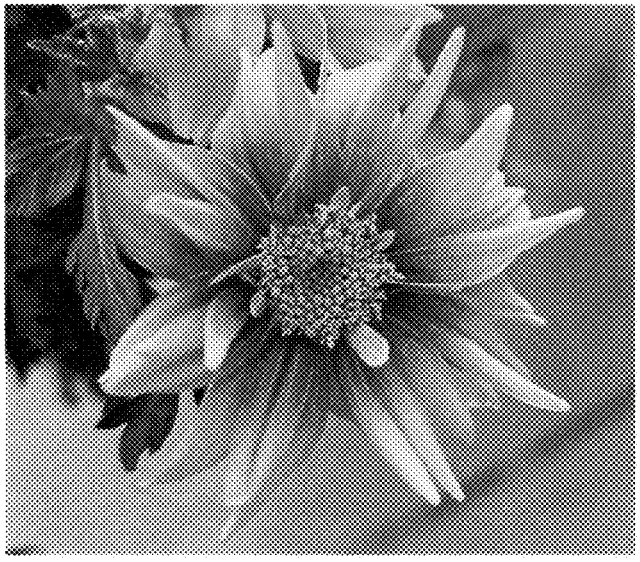
FIG. 2 illustrates a close-up view of an individual inflorescence of 'Balbidbador'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2023 under natural light conditions in Naperville, Illinois.

The following descriptions and measurements describe approximately 5-month-old plants produced from cuttings from stock plants and grown in a polycarbonate greenhouse under conditions comparable to those used in commercial practice. The plants were grown in West Chicago, Illinois in 4.5-inch containers for approximately 4 months utilizing a soilless growth medium. Plants were given one pinch at transplant. Greenhouse temperatures were maintained at approximately 68° F. to 70° F. (20° C. to 21° C.) during the day and approximately 60° F. to 65° F. (16° C. to 18° C.) during the night. Supplemental lighting was used. Measurements and numerical values represent averages of typical plants.

Botanical classification: *Bidens ferulifolia* 'Balbidbador'.

Parentage:

*Female and male parents.*—Proprietary *Bidens ferulifolia* breeding selection coded BID-1490-002, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous, medium to thin in thickness.

*Rooting habit.*—Freely branching, dense.

Plant description:

*Commercial crop time.*—Approximately 5 to 7 weeks from a rooted cutting to finish in a 10 cm container.

*Growth habit and general appearance.*—Moderately vigorous, compact, semi-upright.

*Size.*—Height from soil level to top of plant plane: Approximately 14.0 cm. Width: Approximately 49.0 cm.

*Branching habit.*—Freely branching, pinching improves lateral branching. Quantity per plant: Approximately 7.

*Branches.*—Strength: Strong. Shape: Round in cross section. Length: Approximately 23.0 cm. Diameter: Approximately 3.0 mm to 5.0 mm. Length of central internode: Approximately 1.2 cm. Texture of young and mature stems: Densely pubescent. Color of young stems: Closest to 146B often with an overlay of 187A. Color of mature stems: Closest to N186C.

Foliage description:

*General description.*—Form: Trifoliate. Quantity per branch: Approximately 26. Arrangement: Opposite. Fragrance: None detected. Aspect: Petiole is acute angle to stem; blade is perpendicular to stem or downward turning.

*Leaves.*—Shape of leaf and leaflets: Ovate. Margin of leaf and leaflet: Laciniate. Apex of leaf and leaflet: Acuminate. Base of leaf and leaflet: Attenuate. Venation pattern: Pinnate. Length: Approximately 3.3 cm. Width: Approximately 3.0 cm. Length of terminal leaflet: Approximately 2.4 cm. Width of terminal leaflet: Approximately 1.6 cm. Length of lateral leaflet: Approximately 1.5 cm. Width of lateral leaflet: Approximately 1.1 cm. Texture of upper and lower surfaces: Sparsely pubescent. Color of upper surface of young and mature foliage: 137A with venation slightly darker than leaf lamina except for midvein of 146D tinted with 187A at base. Color of lower surface of young and mature foliage: Closest to 138A with venation slightly darker than leaf lamina except for midvein of 146D. Length of rachis: Approximately 3.0 mm. Diameter of rachis: Approximately 1.0 mm. Texture of upper and lower surfaces of rachis: Moderately pubescent. Color of upper and lower surfaces of rachis: 146D with an overlay of 187A.

*Petiole.*—Length: Approximately 8.0 mm. Diameter: Approximately 1.5 mm. Texture of upper and lower surfaces: Densely pubescent. Color of upper and lower surfaces: 146D with an overlay of 187A.

Flowering description:

*Flowering habit.*—'Balbidbador' is freely flowering under outdoor growing conditions with substantially continuous blooming from early spring through autumn.

*Lastingness of individual inflorescence on the plant.*—Approximately 3 to 4 weeks.

Inflorescence description:

*General description.*—Type: Solitary, composite, double-type. Shape: Radiant head. Aspect: Facing upward and outward. Arrangement: Terminal, held upright on strong peduncles. Fragrance: Slight. Quantity per plant: Approximately 16. Diameter: Approximately 5.0 cm. Depth: Approximately 3.5 cm.

*Peduncle.*—Strength: Strong. Aspect: Erect to approximately 45° from vertical. Length: Approximately 4.0 cm to 5.5 cm. Diameter: Approximately 1.5 mm. Texture: Densely pubescent. Color: 146B occasionally with an overlay of 187A.

*Bud just before opening.*—Quantity per plant: Approximately 7. Shape: Oblate. Diameter: Approximately 8.0 mm. Depth: Approximately 5.0 mm. Color: 146C.

*Ray florets.*—Quantity per inflorescence: Approximately 8, with 1 to 3 irregularly shaped petaloids per ray floret. Arrangement: In a single whorl, imbricate. Aspect: Perpendicular to disc, subtending with age. Shape: Ovate. Appearance: Dull. Margin: Entire. Apex: Three lobed to incised. Base: Rounded. Length: Approximately 2.2 cm. Width: Approximately 1.3 cm. Petaloid length: Approximately 2.0 mm to 2.2 cm. Petaloid width: Approximately 3.0 mm. Texture of upper surface: Glabrous. Texture of lower surface: Glabrous, with two longitudinal ribs. Color of upper surface when first open: 14A with a heavy overlay of N34A on approximately lower half. Color of lower surface when first open: 14B with faint underlay of N34A on approximately lower half. Color of upper surface when fully open: 14A with an overlay of N34A on approximately lower half, overlay fades with age. Color of lower surface when fully open: 14B with faint underlay of N34A on approximately lower half.

*Disc florets.*—Disc diameter: Approximately 1.1 cm. Quantity per inflorescence: Approximately 95. Arrangement: Spirally arranged in center of inflorescence. Shape: Tubular. Margin of free portion: Entire. Apex: Five acute tips. Base: Fused into a tube. Length: Approximately 8.0 mm. Diameter: Approximately 1.0 mm. Texture of inner surface: Glabrous. Texture of outer surface: Sparsely pubescent near base. Color of upper or inner surface when first and fully open: 17C. Color of lower or outer surface when first and fully open: 17C with tips of 17B and base of 145D.

*Receptacle.*—Shape: Flat disc. Diameter: Approximately 5.0 mm. Color: 145D.

*Phyllaries.*—Quantity per inflorescence Approximately 12. Arrangement: In two whorls. Appearance: Dull. Shape: Lanceolate. Margin: Entire. Apex: Acute. Base: Truncate. Length: Approximately 1.1 cm. Width: Approximately 1.0 mm. Texture of upper or inner surface: Sparsely pubescent. Texture of lower or outer surface: Moderately pubescent. Color of upper and lower surfaces: 137A.

*Reproductive organs.*—Androecium: Present on disc florets only. Stamen quantity: 5 per floret. Anther shape: Oblong, basifixed. Anther length: Approximately 2.0 mm. Anther color: 166A. Filament length: Approximately 3.0 mm. Filament color: Closest to NN155A, translucent. Pollen amount: Sparse. Pollen color: 23A. Gynoecium: Present on disc florets only. Pistil quantity: 1 per floret. Pistil length: Approximately 8.0 mm. Stigma shape: Bifurcate, strongly curled. Stigma length: Approximately 1.0 mm, 2.0 mm if straightened. Stigma color: 17B. Style length: Approximately 5.0 mm. Style color: 154D, translucent. Ovary length: Approximately 2.0 mm. Ovary color: 145D.

Seed and fruit production: Neither seed nor fruit production has been observed.

Disease and pest resistance: Resistance to pathogens and pests common to *Bidens* has not been observed.

What is claimed is:

1. A new and distinct cultivar of *Bidens* plant named 'Balbidbador', substantially as herein illustrated and described.

* * * * *